United States Patent [19]
Doxsey

[11] Patent Number: 5,972,626
[45] Date of Patent: Oct. 26, 1999

[54] CANCER DETECTION BY CENTROSOME ABNORMALITY

[75] Inventor: Stephen J. Doxsey, Worcester, Mass.

[73] Assignee: University of Massachusetts, Boston, Mass.

[21] Appl. No.: 08/903,158

[22] Filed: Jul. 30, 1997

[51] Int. Cl.⁶ .................. G01N 33/53; G01N 33/563; A61K 39/395; C07K 16/00
[52] U.S. Cl. .................. 435/7.2; 424/138.1; 436/512; 436/513; 530/387.1; 530/387.7
[58] Field of Search .................. 424/9.1, 130.1, 424/138.1, 178.1; 435/4, 7.21, 40.5, 325, 366

[56] References Cited

PUBLICATIONS

Winey, M., Genome stability: Keeping the centrosome cycle on track, Curr. Biol vol. 6, pp. 962–964, Aug. 1, 1996.
Doxsey et al, Pericentrin, a Highly Conserved Centrosome Protein Involved in Microtubule Organization, Cell vol. 76, pp. 639–650, Feb. 25, 1994.
Hunyady et al, Immunohistochemical Sgnal Amplification by Catalyzed Reporter Deposition and Its Application in Double Immunostaining, J. Histochem. Cytochem. vol. 44 No. 12, pp. 1353–1362, Dec. 1, 1996.
Hollstein et al, p53 Mutations in Human Cancers, Science vol. 253, pp. 49–53, Jul. 5, 1991.
Lingle et al., "Centrosome Hypertrophy in Human Breast Tumors: Implications for Genomic Stability and Cell Polarity", Proc. Natl. Acad. Sci. USA 95:2950–2955, 1998.
Murnane, "Cell Cycle Regulation in Response to DNA Damage in Mammalian Cells: A Historical Perspective", Cancer and Metastasis Reviews 14:17–29, 1995.
Salisbury, "Centrin, Centrosomes, and Mitotic Spindle Poles", Current Opinion in Cell Biology 7:39–45, 1995.
Archer et al., "Deconstructing the Microtubule–Organizing Center", Cell 76:589–591, 1994.
Byers et al., "Duplication of Spindle Plaques and Integration of the Yeast Cell Cycle", Cold Spring Harbor Symposia on Quantitative Biology XXXVIII:123–131, 1974.
Calarco–Gilliam, "Centrosome Development in Early Mouse Embryos as Defined by an Autoantibody Against Pericentriolar Material", Cell 35:621–629, 1983.
Clayton et al., "Microtubule Nucleating Sites in Higher Plant Cells Identified by an Auto–Antibody Against Perticentriolar Material", J. Cell Biol. 1010:319–324, 1985.
Doxsey et al., Pericentrin, pp. 118–119, in Guidebook to the Cytoskeletal and Motor Protein (Kreis et al., eds., Oxford University Press, Oxford, 1993).
Doxsey et al., "Pericentrin, a Centrosome Protein Involved in the Organization of Microtubules in Meiosis and Mitosis", J.Cell Biol. 111:172a, Abstract 998, 1991.
Doxsey et al., "Pericentrin, a Highly Conserved Centrosome Protein Involved in Microtubule Organization", Cell 76:639–650, 1994.

Doxsey et al., "A Centrosome Protein Involved in Meiotic Spindle Formation", J. Cell Biology 111:179a, Abstract 990, 1990.
Fukasawa et al., "Abnormal Centrosome Amplification in the Absence of p53", Science 271:1744–1747, 1996.
Gard et al., "Centrosome Duplication Continues in Cycloheximide–treated Xenopus Blastulae in the Absence of a Detectable Cell Cycle", The Journal of Cell Biology 110:2033–2042, 1990.
Kalt et al., "Molecular Components of the Centrosome", Trends in Cell Biology, 3:118–128, 1993.
Kellogg et al., "The Centrosome and Cellular Organization", Annual Review of Biochem., 63:639–674, 1994.
Nakamura et al., "Improvement of Assays for Detecting Auto Antibodies", J. Clin. Lab. Anal., 8:360, 1994.
Raff et al., "Nuclear and Cytoplasmic Mitotic Cycles Continue in Drosophila Embryos in which DNA Synthesis Is Inhibited with Aphidicolin", The Journal of Cell Biology 107–2009–2019, 1988.
Rattner et al., "Independence of Centriole Formation and DNA Synthesis", The Journal of Cell Biology 57:359–372, 1973.
Sato et al., "Antihistone Antibodies in Patients with Localized Scleroderma", Arthritis and Rheumatism 36:1137–1141, 1993.
Shero et al., "High Titers of Autoantibodies to Topoisomerase I (Scl–70) in Sera from Scleroderma Patients", Science 231:737–740, 1986.
Stearns et al., "In Vitro Reconstitution of Centrosome Assembly and Function: The Central Role of γTubulin", Cell, 76:623–637, 1994.
Tuffanelli et al., "Anticentromere and Anticentriole Antibodies in the Scleroderma Spectrum", Arch Dermatol. 119:560–566, 1983.
Vazque–Abad et al., "Longitudinal Study of Anticentromere and Antitopoisomerase–I Isotypes", Clin. Immunol. and Immunopath. 74:257–270, 1995.
Vidair et al., "Heat Shock Alters Centrosome Organization Leading to Mitotic Dysfunction and Cell Death", J. Cell. Physiology 154:443–455, 1993.
Zheng et al., "γ–Tubulin Is Present in Drosophila melanogaster and Homo sapiens and Is Associated with the Centrosome", Cell 65:817–823, 1991.
Zheng et al., "Nucleation of microtubule assembly by a γ–tubulin–containing ring complex", Nature 378:578–583, 1995.

*Primary Examiner*—Paula K. Hutzell
*Assistant Examiner*—Timothy A. Worrall
*Attorney, Agent, or Firm*—Fish & Richardson P.C.

[57] ABSTRACT

Disclosed is a method for detecting neoplastic cells in a tissue sample by examining the cells for centrosomal abnormalities such as ectopic localization of centrosomal proteins, hypertrophic centrosomes, and supernumerary centrosomes.

14 Claims, 2 Drawing Sheets

CANCER DETECTION BY CENTROSOME ABNORMALITY

STATEMENT AS TO FEDERALLY SPONSORED RESEARCH

This invention was made with Government support under grant RO1 GM51994 awarded by the National Institutes of Health. The Government has certain rights in the invention.

FIELD OF THE INVENTION

The invention relates to cell biology and oncology.

BACKGROUND OF THE INVENTION

The mitotic spindle in most eukaryotes, including humans, is organized by centrosomes. These organelles nucleate the formation of microtubules that capture chromosomes and segregate the chromosomes into daughter cells at mitosis.

Most cells have a single centrosome throughout most of the cell cycle. Before mitosis, a new centrosome is formed adjacent to the first centrosome. The two centrosomes then form the poles of the mitotic spindle. Upon completion of mitosis and cytokinesis, cells, which transiently have two centrosomes, resolve into two cells, with each containing a single centrosome. Normal cells are rarely observed with more than two centrosomes.

Recently, centrosomal proteins such as pericentrin and γ-tubulin have been identified. Anti-sera raised against these proteins can be used to identify centrosomes and centrosomal components in mammalian cells.

SUMMARY OF THE INVENTION

We have discovered that cells in various cancers, and cell lines derived from cancerous cells, display centrosomal abnormalities.

Based on this discovery, the present invention features a method for detecting neoplastic disease, if present, in tissue from a patient. The method includes obtaining a tissue sample containing multiple cells from the patient, then fixing the tissue sample, contacting the tissue sample with a centrosome detecting antibody under conditions that permit binding of the antibody to a centrosomal antigen in the cells, and then detecting the antibody bound to the centrosomal antigen. The method allows for the detection of centrosomal abnormalities, if present, in the cells of the tissue sample, thereby detecting neoplastic disease in the tissue.

The centrosomal antigen can be a protein present in centrosomes, e.g., pericentrin, cp140, centrin, γ-tubulin, α-tubulin, and β-tubulin. The antibody can be detected by means of a label, e.g., a fluorophore, which can be covalently attached to the centrosome detecting antibody or to a secondary antibody. Alternatively, the label can be a peroxidase.

The antibody can be detected by means of direct or indirect labelling. Examples of direct labelling include covalent attachment of a fluorophore to the centrosome detecting antibody. Examples of indirect labelling include covalent attachment of a fluorophore to a secondary antibody that binds to the centrosome detecting antibody.

The tissue sample can be from any human tissue to be tested for cancer, e.g., the bladder, brain, breast, colon, connective tissue, kidney, lung, lymph node, esophagus, ovary, skin, stomach, testis, and uterus. The tissue sample can be fresh, e.g., a biopsy sample, or can be from an archived sample, e.g., a frozen sample or a sample embedded in paraffin.

Centrosomal abnormalities can appear in various ways, e.g., as ectopic, non-centrosomal localization of centrosomal proteins; as hypertrophic centrosomes, or as supernumerary centrosomes. A tissue sample is scored as neoplastic if a substantial fraction of its cells display centrosomal abnormalities.

Samples can be processed using methods known in the art and can include tissue isolation and dissociation to release individual cells. Cells can be spun onto coverslips ("cytospun"), fixed, and subjected to immunofluorescence staining as described in Doxsey et al., Cell 76:639 (1994).

Any polyclonal antibody or monoclonal antibody that recognizes a centrosomal antigen can be used in the invention. The antibody can be produced so that it recognizes a preselected epitope of a centrosome protein.

Bound antibodies can be detected using detection methods known in the art, e.g., immunofluorescence, immunoperoxidase staining, flow cytometry, or Western blot hybridization.

As used herein, "ectopic localization of centrosomal proteins" means localization of a centrosomal component, e.g., pericentrin, in a cell in a location other than that occupied by a centrosome.

As used herein, "hypertrophic centrosome" means a centrosome having an altered morphology relative to a centrosome in non-cancerous cells, e.g., a diameter twice the size of centrosomes in non-cancerous cells.

As used herein, "supernumerary centrosome" means a centrosome found in a cell that already contains at least two centrosomes.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting.

Various features and advantages of the invention will be apparent from the following detailed description and from the claims.

DETAILED DESCRIPTION

Figure 1:
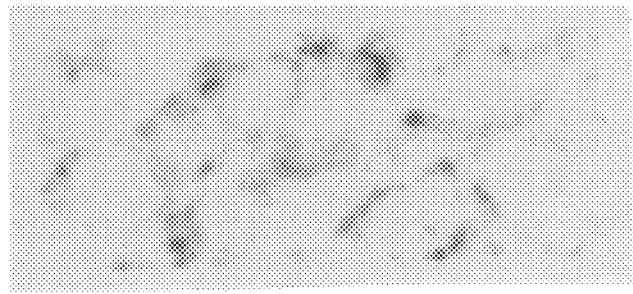
FIG. 1 is a photomicrograph showing immunoperoxidase labeling of metastatic breast tumor cells in a first region of a thin section of a tissue sample from a lymph node. The thin section was incubated with an antibody against pericentrin, then incubated with a secondary antibody conjugated to horseradish peroxidase.

The work leading to this invention has shown that centrosome abnormalities appear in various malignant tumors of different human histogenetic types. Centrosomal abnormalities, in contrast, are essentially absent from corresponding normal tissues.

The present invention provides a simple, rapid, and effective method for detecting cancer cells, if present, in a tissue sample from a human patient. The method is based on our discovery of a positive correlation between the presence of cancer cells and the presence of centrosome abnormalities in these cells, and the absence of detectable centrosome abnormalities in non-cancerous human tissue. A cell is considered to have centrosomal abnormalities, and thus to indicate a cancerous state, if it contains one or more of the following defects: ectopic localization of centrosomal proteins, hypertrophic centrosomes, or supernumerary centrosomes. A tissue sample is typically scored as neoplastic if a substantial fraction of its cells display centrosomal abnormalities.

Antibody Production and Purification

For practicing the present invention, an antibody that recognizes centrosomes is necessary. Antibody specificity for a centrosomal protein is preferable but not required. If an antibody that recognizes a non-centrosomal antigen is used, preferably, the non-centrosomal structure recognized is readily distinguished from a centrosome, e.g., by its cytological staining pattern. A polyclonal antibody or monoclonal antibody suitable for use in the present invention can be obtained according to conventional procedures. See, e.g., Harlow et al., supra, chapters 5–9.

Antibodies that react with centrosomal proteins are known and their preparation has been described. See, e.g., Doxsey et al., Cell 76:639 (1994), describing the preparation of antibodies to pericentrin; and Stearns et al., Cell 76:629 (1994), describing the preparation of antibodies to γ-tubulin; and Salisbury et al., Curr. Opin. Cell Biol. 7:39 (1995), describing the preparation of antibodies to centrin. A number of centrosome proteins are described in Schliwa et al., Trends Cell Biol. 3:377 (1993). Procedures for obtaining antibodies that react with a centrosome protein can be carried out using a preparation of non-human centrosome protein, e.g., murine pericentrin protein. A centrosome protein preparation suitable for eliciting antibodies useful in the present invention can be obtained according to various procedures, including those described by Doxsey et al., (supra).

Antibodies useful in the present invention can also be obtained by immunizing an animal with a preparation containing an intact centrosome protein. Alternatively, useful antibodies can be obtained by immunizing an animal with a polypeptide or oligopeptide corresponding to one or more epitopes on a centrosome protein.

Immunodetection

Numerous known methods for using antibodies to detect a specific protein, including centrosomal proteins such as pericentrin, centrin, and γ-tubulin, in a biological sample are useful in the present invention. In addition, antibodies that detect proteins such as α or β tubulin, that are present in, but not specific for, centrosomes, can be used.

Antibodies recognizing centrosomal antigens can be used individually or in combination as a "cocktail".

A preferred method for detecting binding of a centrosome-recognizing antibody is immunofluorescence analysis. Immunofluorescence analysis advantageously avoids a dilution effect when relatively few cancer cells are in the midst of normal cells. An early step in immunofluorescence analysis is tissue fixation, which preserves proteins in place within cells and preserves the centrosomes within the cells.

Another preferred method for detecting binding of a centrosome-recognizing antibody is immunoperoxidase staining. This can be carried out essentially as described in Hunyady et al., J. Histochem. Cytochem. 44:1353 (1996).

Preferably, when immunofluorescence or immunoperoxidase analysis is employed in the practice of this invention, several thin sections from each tissue sample are prepared and analyzed. This increases the likelihood of finding small tumors.

Another antibody method that can be used to detect centrosome abnormalities is western blot analysis, i.e., sodium dodecyl sulfate-polyacrylamide gel electrophoresis ("SDS-PAGE"), followed by immunoblotting with antibodies recognizing centrosomal antigens.

Immunoassays such as antibody capture assays, two-antibody sandwich assays, and antigen capture assays can also be used in the present invention. Sample preparation for immunoassays includes tissue homogenization. Immunoassays have the advantage of enabling large numbers of samples to be tested relatively quickly, and they offer quantitative precision.

Principles and practice of immunohistochemistry, western blot analysis, and immunoassays are well known. One of ordinary skill in the art can select suitable protocols and carry out immunohistochemical analysis, western blot analysis, or an immunoassay, in the practice of the present invention. For guidance in these techniques, see, e.g., Harlow et al., *Antibodies—A Laboratory Manual*, Cold Spring Harbor, Cold Spring Harbor, N.Y. (1988).

Experimental Results

Tumor Samples and Cell Lines

Cell lines and tumor samples were obtained from the Departments of Pathology and oncology at the University of Massachusetts Medical Center at Worcester, Mass.

Hodgkin's Disease Cell Lines

Some experiments involved a JC cell line, which was a Reed-Sternberg-like cell line grown from an immunocompromized patient with a Hodgkin's disease-like lymphoma. L428 and KHM2 are Hodgkin's disease cell lines obtained from the German Collection of Microorganisms and Cell Cultures. HD70 is a cell line described in Kanzaki et al., Cancer 69:1034 (1992) and was obtained from Ichiro Kubonishi. All cells were grown in RPMI1640 media containing 20% FCS, penicillin, and streptomycin.

Breast Carcinoma Cell Lines

The HS578T and MDA-MB-436 cell lines were grown in Leibovitz L-15 media with 20% FCS, 0.25 IU/ml insulin, 45 mg/ml glucose, penicillin, and streptomycin. The BT-549 lines were grown in RPMI 1640 with 10% FCS, penicillin, and streptomycin.

Colon Carcinoma Cell Line

Color carcinoma cell line HT-29 was grown in McCoy's 5A medium with 10% FCS, penicillin and streptomycin.

Lymphoblastoid B Cell Lines

B115 and B218 are lymphoblastoid B cell lines prepared by John Sullivan (University of Massachusetts Medical Center, Worcester, Mass.) from peripheral blood B cells and grown in PRMI1640 media containing 20% FCS, penicillin and streptomycin.

Other Cell Lines

COS, CHO, and NIH 3T3 cells were grown as described by (ATCC).

Antibodies

Pericentrin anti-sera were raised in rabbits as described in Doxsey et al., Cell 76:639 (1994). The pericentrin anti-sera were used at a dilution of 1:1000. Monoclonal antibodies specific for anti-γ-tubulin, centrin, or α-tubulin were used at dilutions of 1:2000, 1:500 and 1:1000, respectively. Anti-rabbit secondary antibodies were used with the pericentrin anti-sera and anti-mouse secondary antibodies were used in conjunction with the antibodies to γ-tubulin, centrin, and α-tubulin.

For most intense staining, primary antibodies were collectively visualized by using secondary antibodies conjugated to the same fluorophore e.g., cy3.

EXAMPLE 1

Preparation of Archival Tissues for Determination of Centrosome Abnormalities

Archival material consisted of biopsy material that was 2 weeks to 23 years old. The material had been fixed in 10% formaldehyde/PBS for 4–24 hours prior to embedding in paraffin.

Tissue sections (5 micrometer thickness) were cut on a conventional microtome and used for paraffin-embedded tissue sectioning. Sections were floated on a 37° C. water bath, picked up on glass slides, air-dried, and baked at 60° C. overnight.

Sections were deparaffinized in xylenes and then transferred into 100% ethanol. Sections were rehydrated in a gradient of ethanol/water solutions containing a progressively lower ethanol concentration to a final ethanol concentration of 70%. Sections were then transferred to PBS and kept at 4° C. until immunostaining.

EXAMPLE 2

Preparation of Cells from Fresh Tissues for Determination of Centrosome Abnormalities Cells were processed essentially as described in Howard et al., Cytometry 19:146 (1995). Cell suspensions were removed from surgical resection specimens of carcinomas and sarcomas by removing small samples (5 mm square) of tissue and then mincing the samples with a razor blade in PBS at room temperature. Minced tissue was then washed in PBS and resuspended in 1 ml aliquot of PBS containing 1.0 U/ml of collagenase (Sigma Chemical Co., St. Louis, Mo.) and 0.1 U/ml DNase I (Sigma Chemical Co., St. Louis, Mo.), and then incubated for 2 hours at room temperature. During the incubation, the samples were rotated end over end.

Following collagenase and DNase digestion, the samples were strained on a 100 micrometer nylon filter (Nytex, Small Parts, Inc., Miami Lakes, Fla.), pelleted, washed in PBS, by sequential centrifugation at 325 g. Then they were cytospun onto slides, as described below. EXAMPLE 3

Preparation of Blood Tumor Cells for Determination of Centrosome Abnormalities

Leukemia and lymphoma cells were obtained from peripheral blood, bone marrow, and lymph nodes from a clinical flow cytometry laboratory, after conventional clinical workup.

Mononuclear cells were isolated by centrifugation on Ficoll (Sigma) density gradients as according to the Ficoll vendor's recommendations. The cells were then washed twice by centrifugation at 500 g in Minimal Enriched Media (MEM) containing 5% bovine calf serum, and cytospun onto slides as described in Example 4 (below).

EXAMPLE 4

Preparation of Suspension Cells for Determination of Centrosome Abnormalities

Approximately $2 \times 10^5$ suspension cells (cells released from tumors by digestion or any cell free in a buffer solution, e.g., collected as in Example 3) were resuspended in 100 microliters of PBS at room temperature and placed in a cytospin funnel (Shandon, Inc.). Cytofunnels were attached to slides and spun at room temperature for 5 minutes at 65 rpm in a clinical Cytocentrifuge (Cytp 2, Shandon, Inc.). Cells were then fixed, processed, and mounted as described in Doxsey et al., supra, except that cells were often stored in MeOH for 12–24 hours before staining.

EXAMPLE 5

Immunofluorescence Labeling of Tissues and Cells to Examine for the Presence of Centrosome Abnormalities Cells were prepared for immunofluorescence labeling essentially as described in Doxsey, et al., Cell 76:639 (1994). Cells were grown on 12 mm glass coverslips or cytospun onto glass slides. Cells were washed in PBS by placing coverslips into 12 well plates (Costar) with 1–2 ml of PBS or by immersing slides in Coplin jars filled with PBS.

In some cases, cells were permeabilized (to release soluble proteins and better visualize centrosome staining) by aspirating off the PBS and adding permeabilization buffer (80 mM Pipes pH 6.8, 5 mM EGTA, 1 mM $MgCl_2$, 0.5% TX-100) to plates or Coplin jars, and then incubating for 60 seconds at room temperature.

Coverslips were immediately transferred to slides or to new container/plates with −20° C. methanol and incubated for 5 minutes (samples can be stored for days in methanol kept at −20° C.).

To perform immunofluorescence staining, cells were rehydrated and incubated with a blocking solution by removing one-half volume of the methanol solution, taking care to ensure that some methanol remained on the cells in order to avoid desiccation. Cells were then washed 5 times in PBS by replacing half the volume of the previous wash solution with a half volume of the new wash solution. After the last wash, a half volume of blocking solution (blocking solution is PBSAT: 1X PBS, 0.5% Triton X-100 (Sigma), 2% bovine serum albumin (BSA, Sigma) was added and incubated for 10 minutes. The blocking solution was replaced with fresh PBSAT, and the cells were incubated an additional 10 minutes.

Coverslips or slides were placed (cell-side up) in a moist chamber on parafilm and covered with PBSAT. A moist chamber was prepared by covering the outer side of a 150mm tissue culture plate with aluminum foil to block light, covering the bottom inside chamber with parafilm, and placing a piece of wet paper towel in the plate to maintain moisture inside the plate.

The PBSAT blocking solution was removed, and primary antibody diluted in PBSAT was added and incubated for 1 hour at room temperature. The antibody was added at a volume of 25–35 μl/coverslip or 120 μl/slide. Following incubations, the samples were washed in PBSAT 10 times by aspirating solution, adding PBSAT (~0.5 ml/coverslip or 2 ml/side).

A fluorochrome-conjugated secondary antibody raised against the appropriate species (see Antibody section) was then added and incubated for 20 minutes at room temperature. The secondary antibody was usually added at a dilution of 1:500 as recommended by the vendor and at the same volumes as used for the primary antibody. Following the incubation, the samples were washed 10 times in PBSAT.

Nuclear staining was performed using 20 ul/coverslip or 100 ul/slide of a $10^{-4}$ dilution in PBSAT of a 5 mg/ml stock solution of DAPI (Sigma). Following a 1 minute incubation with the DAPI solution, cells were washed 5 times in PBSAT 5 times, then twice in PBS. Prior to mounting, the samples were dipped twice in double distilled water and partially drained.

Coverslips were mounted by placing an inverted coverslip (cell side down) on clean glass slide using glycerol-based mounting medium with antifade (Vectashield, Vector Labs, Calif.). Slides were mounted by placing a drop of Vectashield on slide and inverting the clean coverslip on slide. Excess mounting solution was aspirated from around the edges of coverslip, and the coverslips were sealed with nail polish.

EXAMPLE 6

Immunoperoxidase Labeling of Tissues and Cells to Examine the Presence of Centrosomal Abnormalities Samples for immunoperoxidase labeling were processed essentially as described in Norton et al., J. Pathol. 173:371 (1994). Slides containing tissue sections or cells, prepared as described above, were pressure-heated in antigen retrieval solution (1 mM EDTA) in a microwavable pressure cooker (Nordic Ware) for 20 minutes, allowed to cool to room temperature, and transferred to PBS. The cooled slides were immersed in 3% $H_2O_2$ in PBS for 15 minutes, to block endogenous peroxidase. The slides were then processed for immunoperoxidase detection using a commercial kit (TSA-Indirect Kit, NEN Life Science Products). For details regarding immunoperoxidase detection, see J. Histochem. Cytochem. 44:1353 (1996). Aliquots (100 microliter) of TNB blocking buffer containing a 1:1000 dilution of the pericentrin antibody were added to the slides for 1 hour at room temperature. Slides were then washed in TNT buffer (TSA-Indirect Kit, NEN Life Science Products) three times, for five minutes each.

Biotinylated secondary antibody against rabbit immunoglobulins (Ventana Medical Systems) diluted 1:1000 was applied for one hour to the slides and they were incubated as above, after which they were washed in TNT buffer three times for five minutes each.

Signals were amplified by subjecting the slides to catalyzed reporter deposition (Tyramine Signal Amplification, TSA-Indirect Kit, NEN Life Science Products) according to the vendor's instructions. Slides were then washed in NBT buffer, counterstained in hematoxylin, and mounted in Permount (Sigma) as described by the manufacturer.

To detect immunoperoxidase labeling, cells were visually examined using a conventional light microscope equipped with 25-100X lenses.

Centrosome Abnormalities

Using the methods described in Examples 1–6 (above), examination of centrosomes enabled reliable visual distinction of cancerous tissue from noncancerous tissue, on the basis of centrosome abnormalities. The observed abnormalities included ectopic localization of centrosomal proteins, hypertrophic centrosomes, and supernumerary centrosomes.

Figure 2:
FIG. 2 is a photomicrograph showing immunoperoxidase labeling of nontumor cells in a second (noncancerous) region of the thin section, a cancerous region of which is shown in FIG. 1.

Examples of centrosomal staining patterns in cancer and non-cancer cells are shown in FIGS. 1–7. FIG. 1 shows ectopic localization of centrosomal proteins in a thin section of cells in a cancerous region of a biopsy sample. Labelling throughout the cytoplasm, which is characteristic of ectopic localization of centrosomal proteins, is observed in the cells visible in FIG. 1. In contrast, FIG. 2 shows that cells in a thin section of a noncancerous region of the same biopsy sample show a single small focus of staining that is typical of normal centrosomes.

Figure 3:
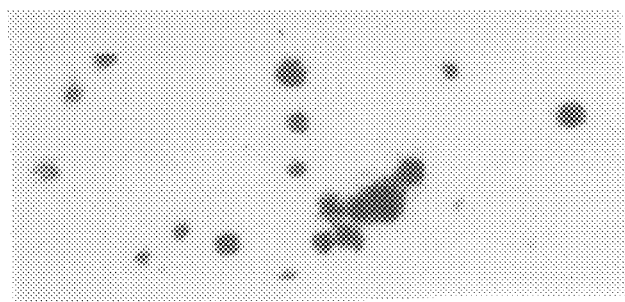
FIG. 3 is a photomicrograph showing immunoperoxidase labeling of glioblastoma multiforme tumor cells in a first region of a thin section of a tissue sample taken from brain. The thin section was incubated with an antibody to pericentrin, then incubated with a secondary antibody conjugated to horseradish peroxidase.
Figure 4:
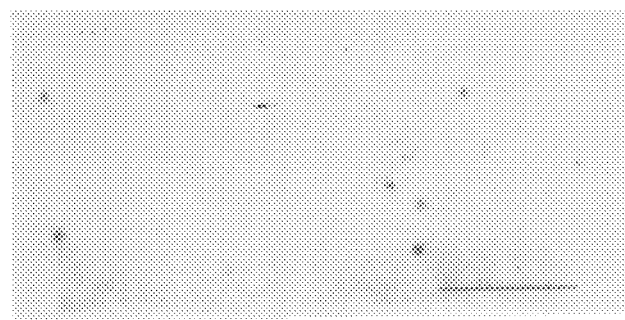
FIG. 4 is a photomicrograph showing immunoperoxidase labeling of nontumor cells in a second (noncancerous) region of the thin section, a cancerous region of which is shown in FIG. 3.

FIG. 3 illustrates cells in a thin section of a cancerous region of a biopsy sample showing centrosomes having both hypertrophic and supernumerary abnormalities. The hypertrophic phenotype is revealed by the large centrosomes in the cells. For comparison, FIG. 4 shows normal-size centrosomes in cells of a non-cancerous region of the same biopsy sample used in FIG. 3. The multiple centrosomes observed are characteristic of supernumerary centrosomes.

Figure 5:
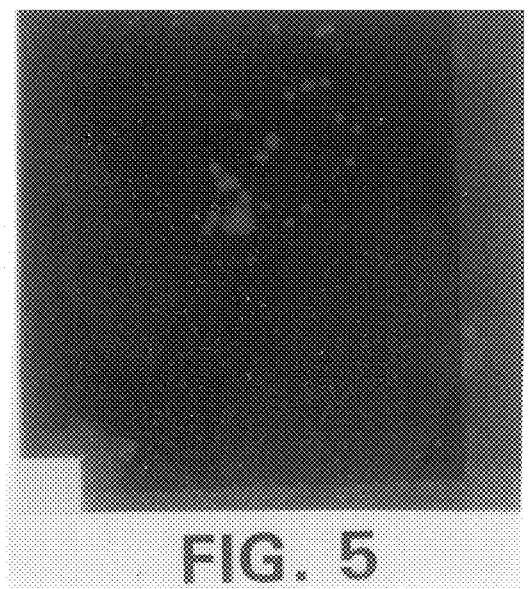
FIG. 5 is a photomicrograph showing immunofluorescence labeling of a cell from a breast cancer line MDA-MB-157 incubated with an antibody to pericentrin, then incubated with a secondary antibody conjugated to fluorescein. DAPI staining was used to visualize the DNA, which is revealed by the blue image.
Figure 6:
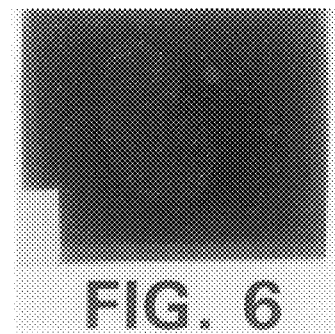
FIG. 6 is a photomicrograph showing immunofluorescence labeling of a cell from a Chinese Hamster Ovary cell line incubated with an antibody to pericentrin, then incubated with a secondary antibody conjugated to fluorescein. DAPI staining was used to visualize the DNA, which is revealed by the blue image.
Figure 7:
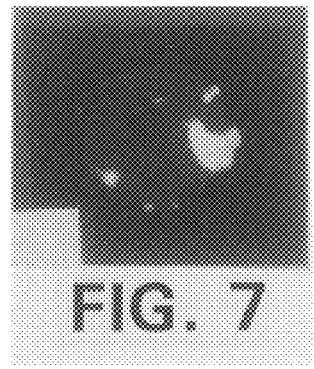
FIG. 7 is a photomicrograph showing immunofluorescence labeling of a cell from a breast tumor biopsy incubated with an antibody to pericentrin, then incubated with a secondary antibody conjugated to fluorescein. DAPI staining was used to visualize the DNA, which is revealed by the blue image.

Supernumerary centrosomes detected using immunofluorescence labeling are shown in FIGS. 5 and 7. FIG. 5 is a single cell from a breast cancer line showing over 25 centrosomes, which appear as multiple, punctate images. FIG. 7 shows a single cell from a breast tumor biopsy showing multiple centrosomes in green/white images. In contrast, FIG. 6 demonstrate that a single centrosome is seen in a control, noncancerous cell.

Data from solid tumors from breast, prostate, brain, lung, colon cancers, as well as non-neoplastic tissues are shown in Table 1. Data were compiled from 17 separate preparations and staining reactions. Evidence of centrosomal abnormalities was detected using anti-pericentrin antibodies and immunoperoxidase visualization of the bound antibody. A tissue sample was scored as having supernumerary centrosomes, hypertrophic centrosomes, or ectopic localization of centrosomal proteins if more than 10 percent of the cells in a field showed any of the these properties. More than one centrosomal defect was often detected in a particular cell.

In contrast, no centrosomal defects were detected in cells from non-neoplastic tissues. The data for non-neoplastic tissues were complied from stromal cells, lymphocytes, astroglia or epithelial cells. The majority (more than 95%) had centrosomes typical of other non-neoplastic cells. Occasionally, control cells appeared to contain supernumerary centrosomes; however, in these cases, which represented less than 5% of the cells in a population, it was difficult to determine whether supernumerary centrosomes were present or whether some of the centrosomes were in a superimposed adjacent cell.

Centrosomal abnormalities were also examined in tumor-derived cell-lines, as shown in Table 2. In these experiments, centrosomal abnormalities were determined solely by scoring cell populations for supernumerary centrosomes, i.e., by counting the number of centrosomes in the cells. The cell lines were derived from colorectal and breast carcinomas, and Hodgkin's lymphoma, as indicated in the Table 2. For the cell lines in Table 2, 750–5000 cells were examined for each cell line, and cells were scored as having abnormal centrosomes if more than 5% of the cells in the population showed supernumerary centrosomes. The incidence of abnormal centrosomes in tumor lines was 17–67%, whereas the incidence of supernumerary centrosomes in non-tumor lines was 0.05 to 1.0%.

A summary of tumor types and cell lines in which centrosomal abnormalities in more than 20 sample preparations have been detected is shown in Table 3. We have also detected centrosomal abnormalities in other tumor types, such as sarcomas.

Most of the invasive breast carcinomas and breast cancer cell lines had amplified centrosomes. Up to 35% of the cells in some breast tumors and cell lines exhibited centrosome amplification, and it was not uncommon to find a 20-fold increase in centrosome number. This was in contrast to cells in tissues adjacent to breast tumors, cells from cancer-free individuals, and most non-cancer cell lines, where one or two centrosomes were consistently observed.

TABLE 1

Centrosome Abnormalities in Primary Solid Tumors

| | Breast Tumor | Prostate Tumor | Brain Tumor | Lung Tumor | Colon Tumor | Non-neoplastic control |
|---|---|---|---|---|---|---|
| Cumulative Abnormalities; | 18/19 | 16/19 | 19/20 | 15/15 | 13/15 | 0/88 |
| Individual Defects: | | | | | | |
| Supernumerary Centrosomes | 16/19 | 15/18 | 18/20 | 15/15 | 6/15 | 0/88 |
| Hypertrophic Centrosomes | 12/19 | 14/18 | 6/20 | 6/15 | 6/15 | 0/88 |
| Ectopic Localization of Centrosomal Proteins | 14/19 | 10/18 | 9/20 | 8/15 | 13/15 | 0/88 |

In Table 1, "Cumulative Abnormalities" represents the total number of tumors that exhibited one or more individual defects by immunoperoxidase staining. "Supernumerary Centrosomes" refers to the numbers of fields of cells in which more than 10% of the cells had three or more centrosomes. "Hypertrophic Centrosomes" refers to the numbers of fields of cells in which more than 10% of the cells had centrosomes that were at least two-fold larger in diameter than those in surrounding stromal cells or non-neoplastic epithelial cells in the same tissue section. "Ectopic Localization of Centrosomal Proteins" refers to the numbers of fields of cells in which more than 10% of the cells in the field showed ectopic localization of centrosomal proteins.

Non-neoplastic cells used as internal controls for each case included stromal cells, lymphocytes, astroglia or epithelial cells. The majority (>95%) had centrosomes typical of other non-neoplastic cells. The data shown in Table 1 were compiled from 17 separate preparations and staining reactions.

TABLE 2

Centrosome Abnormalities in Tumor-Derived Cell Lines

| Cells and Cell Lines | Tissue of Origin | Abnormal Centrosomes |
|---|---|---|
| Tumor-derived cell lines: | | + |
| HT-29 | Colorectal | + |
| HS578T | Breast | + |
| BT-549 | Breast | + |
| MDAMB436 | Breast | + |
| L428 | Hodgkins | + |
| KHM2 | Hodgkins | + |
| JC | Hodgkins | + |
| HD70 | Hodgkins | + |
| Control Cells (human): | | |
| B115 | Lyphoblastoid | – |
| B218 | Lyphoblastoid | – |
| Control Cells (other): | | |
| NIH3T3 | Mouse | – |
| CHO | Hamster ovary | – |
| COS-7 | Monkey kidney | – |

TABLE 3

Summary of Tumor Typed and Cell Lines Tested

| Carcinomas | |
|---|---|
| Breast | Infiltrating ductal carcinomas of the breast |
| Prostate | Invasive prostate carcinomas |
| Colon | Invasive colon carcinomas |
| Lung | Nonsmall cell lung carcinomas |
| | Squamous cell carcinomas |
| | Adenocarcinomas |
| | Large cell carcinomas |
| Brain | |
| Ovarian | |
| Stomach | Adenocarcinoma of the stomach |
| Lymphomas & Leukemias | |
| Hodgkin's lymphomas | |
| Large cell B lymphomas | |
| Acute myeloid leukemias | |
| Chronic myelogenous leukemias | |
| Myelodysplastic syndrome (pre-leukemic) | |
| Cell lines derived from: | |
| Colorectal carcinomas | |
| Breast carcinomas | |
| Hodgkin's Disease | |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting neoplastic disease, if present, in tissue from a patient, said method comprising the steps of:
   (a) obtaining a tissue sample from said patient, said tissue sample containing a plurality of cells;

(b) fixing said tissue sample;

(c) contacting said tissue sample with a centrosome detecting antibody under conditions that permit binding of said antibody to a centrosomal antigen in said cells;

(d) detecting said antibody bound to said centrosomal antigen, thereby detecting centrosomal abnormalities, if present, thereby detecting neoplastic disease in said tissue, if present.

2. The method of claim 1, wherein said centrosomal antigen a protein selected from the group consisting of periceritrin, cp140, centrin, γ-tubulin, α-tubulin, and β-tubulin.

3. The method of claim 2, wherein said antigen is pericentrin.

4. The method of claim 1, wherein said antibody is detectable by means of a label.

5. The method of claim 4, wherein said label is a fluorophore.

6. The method of claim 5, wherein said fluorophore is covalently attached to said centrosome detecting antibody.

7. The method of claim 5, wherein said fluorophore is covalently attached to a secondary antibody.

8. The method of claim 4, where said label is a peroxidase.

9. The method of claim 1, wherein said neoplastic disease is a carcinoma.

10. The method of claim 9, wherein said carcinoma is a colorectal carcinoma or breast carcinoma.

11. The method of claim 1, wherein said neoplastic disease is a sarcoma, leukemia, or lymphoma.

12. The method of claim 1, wherein said centrosomal abnormality is one or more supernumerary centrosomes.

13. The method of claim 1, wherein said centrosomal abnormality is one or more hypertrophic centrosomes.

14. The method of claim 1, wherein said centrosomal abnormality is ectopic localization of one or more centrosomal proteins.

* * * * *